United States Patent [19]

Herstein

[11] Patent Number: 5,217,641
[45] Date of Patent: Jun. 8, 1993

[54] EYE MAKEUP REMOVER

[76] Inventor: Morris Herstein, P.O. Box 209, Scarsdale, N.Y. 10583

[21] Appl. No.: 746,914

[22] Filed: Aug. 19, 1991

[51] Int. Cl.$^5$ ................................................ C11D 7/50
[52] U.S. Cl. .................................... 252/171; 252/172; 252/174.15; 252/DIG. 5
[58] Field of Search ................ 252/171, 172, 174.15, 252/DIG. 5

[56] References Cited

U.S. PATENT DOCUMENTS

| | | | |
|---|---|---|---|
| 4,685,930 | 8/1987 | Kasprzak | 252/171 X |
| 4,960,533 | 10/1990 | Wisniewski et al. | 252/174.15 X |
| 5,011,681 | 4/1991 | Ciotti et al. | 252/174.15 X |
| 5,091,105 | 2/1992 | Madore et al. | 252/174.15 X |

Primary Examiner—Patrick P. Garvin
Attorney, Agent, or Firm—Handal & Morofsky

[57] ABSTRACT

A cyclomethicone-based oil-free, non-stinging make-up remover is disclosed which is effective in removing both aqueous and waterproof make-up. A preferred composition comprises a major proportion of a cyclomethicone compound with a mixture of ester of a medium chain aliphatic alcohol being the benzoates and octanoates of primary alcohols having from 12 to 15 carbon atoms. A tri-alkyl citrate is an optional co-solvent.

12 Claims, No Drawings

EYE MAKEUP REMOVER

TECHNICAL FIELD

The present invention relates to an improved cosmetic composition being an eye make-up remover capable of removing waterproof makeup for example waterproof mascara, as well as eye shadow, foundations, eye liners, lipstick and the like.

BACKGROUND

Make-up removers generally fall into one of two classes: hydrophilic detergent-based removers or hydrophobic oil-based removers. Customarily a make-up remover is selected for use according to the nature of the make-up to be removed, with detergent-based removers being selected for ordinary, emulsion-type make-ups and oil-based removers being used for more permanent types of makeup including, but not limited to, waterproof eye make-ups, for example waterproof mascara and eye shadow, and -waterproof lipsticks. In some cases it may be necessary or desirable to use both types of make-up in sequence to remove an especially durable make-up.

Whereas, known oil-based make-up removers can be quite effective, they suffer from a tendency to deposit an oily residue or film on the wearer's skin. This is particularly undesirable when removing eye make-up because the oil is easily transmitted to the eye, where it may cause discomfort, irritation or blurring of vision.

Oil-free eye make-up removers are known, for example Maybelline Co. "Maybelline 100% Oil Free Eye Make-Up Remover", 1979. However, existing, known oil-free make-up removers tend to cause irritation or stinging owing to the presence of surfactants or detergents or preservatives.

Attempts have been made to formulate oil-free eye make-up removers that are gentle, and do not irritate or sting. For example U.S. Pat. No. 4,390,442 to Quick suggests the use of small quantities of chlorhexidine digluconate and phenethyl alcohol in an aqueous-base buffered cleanser.

In a similar vein, U.S. Pat. No. 4,732,692 to Contamin et al. teaches an aqueous composition in which low concentrations of surfactant, and reduced irritation or stinging are sought by formulating an amphoteric surfactant with an anionic surfactant and a non-ionic or anionic polymer.

U.S. Pat. No. 4,543,205, also to Contamin teaches an aqueous-base eye make-up remover comprising etherous surfactants notably a glucoside alkylether, an amphoteric amidic zwitterion and a third component which can be a polyoxyethylenated sorbitan or glycerol ester or a non-ionic aliphatic ether.

While they may be less irritating, aqueous eye make-up removers according to these proposals are not capable of efficiently and completely removing more durable make-up materials such as waterproof mascara and other waterproof make-ups.

Cyclomethicones are known to be very effective in removing waterproof eye make-up. Also, cyclomethicones are gentle and not liable to sting or irritate. Some of the properties of cyclomethicones are described in a data sheet from Dow Corning entitled "Information About Volatile Silicone Fluids". Here cyclomethicones are described as low-viscosity fluids that are colorless, odorless, nonirritating, volatile cosmetic solvents. They are further described as essentially non-toxic, non-greasy and non-stinging, confirming their suitability for waterproof make-up removal.

However, they are not a commercially practical vehicle to formulate as a major ingredient of a consumer product owing to their volatility: Cyclomethicones have an appreciable vapor pressure at room temperature and therefore cannot be packaged easily using conventional cosmetic packaging, leading to losses on the store shelf or after opening, and a product that is unacceptable to the consumer. These characteristics are also confirmed in the Dow Corning reference by descriptions of their use as base fluids or transient carriers allowing good spreading and easy rub-out and as volatile silicones that evaporate leaving no residue.

Known cyclomethicone-containing, commercial eye make-up formulas contain oils, especially mineral oil, and preservatives or are formulated as two-phase mixtures requiring agitation by the consumer, for example by shaking. One is an aqueous phase including surfactants and preservatives while the other is an oily cyclomethicone phase. While they may be effective eye make-up removers, such formulations are clearly unsatisfactory in that mineral oil-based versions suffer the problem of leaving a troublesome oily residue, as mentioned above, and two-phase formulations are clearly inconvenient and may be misused.

One such product known under the trade mark "Clarion Ultra Pure" from Noxell Corporation, proprietors of a registered trade mark for "ULTRAPURE", comprises cyclomethicone in admixture with mineral oil, paraben preservatives, dioctyl adipate, octyl palmitate and an anti-inflammatory, bisabolol. As previously emphasized, the presence of mineral oil predisposes such formulations to leave an oily residue. Further, their hydrophobicity may render them ineffective in removing aqueous-based make-up and the paraben preservative will cause a stinging sensation in the eyes of most users.

It is one object of this invention to provide an improved cyclomethicone-containing eye make-up remover which is stable, gentle, effective and easy to use.

It is a further object of the invention to provide an improved cyclomethicone-containing eye make-up remover which does not leave an oily film and is effective in removing waterproof make-up such as waterproof mascara, efficiently and substantially completely.

A still further object is to provide an improved cyclomethicone-containing eye make-up remover which is effective in removing aqueous-based make-up as well as waterproof, more hydrophobic make-up.

Still another object of this invention is to provide such an improved cyclomethicone-containing eye make-up remover which is non-stinging and unlikely to irritate the user's eye.

Yet another object of this invention is to provide such an improved cyclomethicone-containing eye make-up remover in a single phase formulation.

SUMMARY OF THE INVENTION

The invention, as claimed, is intended to provide a remedy. It solves the problem of providing a makeup remover that is effective in removing aqueous-based make-up as well as waterproof, more hydrophobic make-up while being stable and non-irritant.

I have found, and the present invention is based on this discovery, that an excellent oil-free make-up remover which overcomes this problem can be prepared by formulating a major proportion of a cyclomethicone or mixture of cyclomethicones with a minor proportion of a cosmetologically acceptable ester of a medium chain aliphatic alcohol or mixture of such esters. The ester or esters used should be miscible with the cyclomethicone material and serve to stabilize it against evaporative losses to give the novel makeup remover of this invention a satisfactory shelf life and aftersale life.

Examples of some preferred classes of non-greasy esters that are effective in practicing this invention, especially when used in combination are the benzoates and octanoates of primary alcohols having from 12 to 15 carbon atoms.

Innocuous cosmetological solvents or co-solvents that do not detract from the properties of the inventive make-up remover formulation can also be included, as can colorants and extenders, so long as they do not significantly detract from the desirable properties of the make-up remover of this invention. A useful example of such a co-solvent is a tri-alkylcitrate. More particularly, tri-octyl citrate is valuable for its ability to impart stability to the make-up remover formulation.

Preferably the makeup remover is substantially oil- or grease-free, and to this end any additional materials that are capable of leaving an oily or greasy residue, especially the ubiquitous mineral oils, are substantially or completely excluded.

Surprisingly, the inventive make-up remover has a valuable combination of characteristics ideally suiting it for its purpose. By following the teaching outlined above, a remover can be produced that is oil-free, clear, odorless and non-toxic, that rubs out easily, is non-irritant, or non-stinging to the eyes, non-greasy to the skin and leaves a dry, smooth feeling on the skin. Furthermore, it can have a good shelf life and can be used by the consumer directly out of the container in which it is supplied without agitation or other pre-treatment and without special storage conditions.

BEST MODE FOR CARRYING OUT THE INVENTION

Some preferred embodiments of the invention including preferred ingredients and formulations will now be described, without implying limitation as to the scope of the invention, and will include a disclosure of the best method known to the inventors of practicing the invention.

A class of cyclomethicone compounds that is preferred for use in the make-up remover of the invention is illustrated by compounds of the formula:

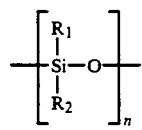

in which $R_1$ and $R_2$ is each lower alkyl having from one to four carbon atoms with or without innocuous substitutes selected from the group consisting of halo, hydroxyl, carboxyl or methoxy and n is from 3 to 6; which compounds are cyclized.

The cyclomethicone material used can be a single one of the foregoing compounds or a mixture thereof and the compound or compounds can be a homopolymer in which all n monomeric units are similar, or a heteropolymer in which they are different.

Some preferred features of the cyclomethicones are that they be homopolymers; that n is 4 or 5; and that $R_1$ and $R_2$ is each methyl. The best known embodiments are octamethylcyclotetrasiloxane and decamethylcyclopentasilloxane.

As described above, the cyclomethicones used in this invention are known to be low viscosity volatile fluids with a low surface tension and a substantial vapor pressure at room temperature. They rub out well, leaving little if any residue and a good clean feel. Rubbing out is typically effected with a cotton ball or other absorbent pad. Again, as previously stated, their volatility gives problems of shelf life both in distribution and for the consumer: Cyclomethicones readily escape, but this problem is solved by the formulation of this invention.

The cosmetologically acceptable ester compounds that are preferred for use in this invention are liquid esters of alcohols having from 8 to 18 carbon atoms, preferably from 12 to 15, with a carboxylic acid selected from the group consisting of benzoic, octanoic, lactic, maleic, citric, and innocuously substituted variants thereof that lack properties such, for example, as toxicity, which would interfere with cosmetological acceptability.

These esters are miscible with cyclomethicones to provide single-phase liquids having improved stability, reduced volatility and elevated boiling points as compared with the cyclomethicones alone.

The best known esters for use in the practice of this invention are esters of what are known in the cosmetics art as $C_{12-15}$ alcohols, with benzoic or octanoic acid, which is to say $C_{12-15}$ alcohols benzoate or octanoate, preferably the 2-ethylhexanoate, being the esters of an alcohol, or alcohols, containing from 12 to 15 carbon atoms with benzoic or octanoic acid.

The benzoate esters are particularly attractive for use in the practice of the present invention because they are not only known cosmetic fluids that exhibit good solvency and are non-toxic and non-irritating but, unlike other distinctly oily fatty acid esters such as isopropyl myristate or octyl palmitate, the esters of $C_{12-15}$ alcohols are substantially devoid of oiliness. While useful, if used alone they are not adequate make-up removers. What is surprising is the combining effect such $C_{12-14}$ alcohols esters have with the defined cyclomethicones in capturing the cyclomethicones in a cosmetic composition that enables their unique make-up removal properties to be utilized in a stable, marketable, easily applied formulation.

The octanoate esters are also especially attractive for use in the practice of this invention and indeed, a preferred embodiment of the invention employs both benzoic and octanoic esters together, preferably the esters of $C_{12-15}$ alcohols. Octanoate esters, especially the preferred ones, are known to be useful cosmetic fluids which are non-toxic and non-irritating. Additionally, they are valuable for the present invention because they are highly stable and, like the benzoic esters described above, miscible with the particular cyclomethicones, also described herein, help retard cyclomethicone volatility, imparting stability thereto and furthermore act as a skin-conditioning agent lending a desirable silky, smooth skin feel to the make-up remover composition of the invention.

"$C_{12-15}$ alcohols" is a term of the art that refers to a mixture of synthetic aliphatic alcohols each having from 12 to 15 carbon atoms which is used in moisturizing creams and lotions, as an emulsion stabilizer and as a viscosity-increasing agent.

Various optional co-solvents and adjuvants may also be used. Especially valuable are co-solvents which though not per se fully effective in removing makeup, being unsatisfactory either for aqueous-based or waterproof makeup removal, do to some degree mimic the properties of cyclomethicone, while having better stability than a cyclomethicone.

Some examples of such co-solvents are liquid triesters of lower aliphatic tribasic carboxylic acids, for example triesters of an alcohol having from 6 to 10 carbon atoms with citric acid, especially trioctyl citrate. The lower aliphatic chain can have from 1 to 6 carbon atoms.

Trioctylcitrate is a non-comedogenic (does not form comedones, blockages of the sebaceous ducts), non-greasy emollient with a similar texture and feel to a cyclomethicone which lacks the validity of a cyclomethicone and with its low freezing point of −50° C., affords excellent stability.

Some preferred proportions, on a weight basis, for practicing this invention are: from 50 to 98%, preferably 60–97% of the cyclomethicone; from 2 to 50%; preferably 5 to 25% of the ester and from 0 to 25%, preferably from 1 to 15% of a co-solvent being a liquid triester of a lower aliphatic tribasic carboxylic acid.

More particularly stated, a preferred embodiment of an oil-free makeup remover composition according to this invention comprises, on a weight basis, from 60 to 97% of a cyclomethicone; from 1 to 15% of an ester of benzoic acid with an alcohol or alcohols containing from 12 to 15 carbon atoms, from 1 to 10% of an ester of octanoic acid with an alcohol or alcohols containing from 12 to 15 carbon atoms and from 1 to 15% of a trioctyl citrate cosolvent.

Preferably, the balance of the makeup remover composition, if any, is made up of innocuous cosmetologically acceptable materials that are grease-free and leave no residue. A particularly preferred embodiment consists substantially exclusively of the materials recited above, with the possible exception of fragrance or coloring, if desired.

What is further surprising about the invention, especially in preferred embodiments, is that the compositions described are effective removers for either normally aqueous-based emulsion-type makeups or oily, waterproof makeups without incorporating conventional cleansers that typically include an amphoteric surfactant.

The present invention, in most embodiments, does not require a surfactant either for cleansing purposes or, being a single phase composition, as a dispersion or emulsifying agent. Surfactants complicate the composition and can be subject to microbial attack, in which case preservatives must also be incorporated, a further complication. Preservatives often sting the eyes.

Thus, the preferred makeup remover compositions according to the invention are not only oil-free, or substantially non-oily, but are also surfactant-free, or preservative-free, or free of either and, accordingly, any balance of ingredients excludes such components from the preferred embodiments.

Consideration of the prior art in the light of these points shows that the invention provides a makeup remover of elegant simplicity with a full complement of properties uniquely suiting it for its purpose.

A particularly preferred embodiment consists substantially exclusively of the materials recited above, with the possible exception of fragrance or coloring, if desired.

Some illustrative embodiments of the invention will now be described, without implying any limitation as to the scope of the invention, with reference to the following Examples.

EXAMPLE 1

80 gm. octamethylcyclotetrasiloxane, 12 gm. $C_{12-15}$ alcohols benzoate and 8 gm. $C_{12-15}$ alcohols octanoate are blended at room temperature in the liquid state for one minute.

EXAMPLE 2

The method of Example 1 is repeated except that the quantity of octamethylcyclotetrasiloxane is reduced to 68 gm. and 12 gm. of trioctylcitrate is included.

EXAMPLE 3

The methods of Examples 1 and 2 are repeated except that decamethylcyclopentasiloxane is used in place of octamethylcyclotetrasiloxane.

PHYSICAL CHARACTERISTICS

The products of Examples 1 to 3 are examined and found to be colorless and odorless single-phase liquids which are stable and do not diminish in volume on storage in conventional packaging.

CHEMICAL CHARACTERISTICS

The products of Examples 1 to 3 are oil-free, free of surfactants or detergents or preservatives, yet not readily degraded by biological agents and are non-aqueous.

COSMETIC CHARACTERISTICS

In tests on human subjects, the products of Examples 1 to 3 are found to be non-greasy, gentle and non-irritating to the skin, with a silky smooth feel. They effectively and apparently substantially completely remove both aqueous and waterproof makeup, including eye makeup, without leaving an oily film or residue. They are found to be capable of repeated use without, in most cases, causing irritation, blurred vision or a stinging sensation in the eyes.

The make-up remover of this invention is effective in removing many or most types of make-up including waterproof mascara, eye shadow, foundations, eye liners, and even lipstick.

TOXICITY AND ALLERGENICITY

When tested for cytotoxicity the products of Examples 1 to 3 show results indicating they are non-toxic to mouse fibroblast cells. Coupled with the known human safety of the ingredients used in Examples 1 to 3, which are proven cosmetic ingredients, these results are strongly suggestive of the human safety of the make-up remover compositions of this invention.

Draize rabbit eye test results on the products of Examples 1 to 3 failed to indicate any ocular irritation. When considered in the context of the known non-irritability of their ingredients, these eye test results suggest that the make-up remover products of this invention are non-irritating for their intended use as make-up remover, especially as waterproof and aqueous-based eye make-up remover.

In summary it has not previously been recognized that a cyclomethicone can be simply formulated to be an effective makeup remover for both aqueous-based and oily, waterproof makeup without unacceptable side effects such as an oily residue or the inconvenience, potential ineffectiveness and complexity of a two-phase composition.

That such an effective formulation can be achieved by simply incorporating an ester of a medium-chain aliphatic alcohol, while excluding conventional oily formulants such as mineral oil, is surprising. The discovery that the ester can not only retard the volatility of a cyclomethicone but also enhance its makeup removing properties is especially valuable.

The term "cosmetologically acceptable" is used to refer to a material that is acceptable for cosmetological use which means that it must be non-toxic, stable, have a satisfactory feel to the skin and be non-irritating to sensitive mucous membranes.

While some illustrative embodiments of the invention have been described above, it is, of course, understood that various modifications will be apparent to those of ordinary skill in the art. Such modifications are within the spirit and scope of the invention, which is limited and defined only by the appended claims.

I claim:

1. A non-aqueous, oil-free make-up remover comprising from 50 to 98% on a weight basis of a cyclomethicone material being a cyclomethicone or a mixture of cyclomethicones, with from 2 to 50% of a cosmetologically acceptable substantially non-oily ester of a medium-chain aliphatic alcohol or mixture of such esters which ester or esters is miscible with said cyclomethicone material and is effective in stabilizing said cyclomethicone material against evaporative losses.

2. A make-up remover according to claim 1 wherein said esters are non-greasy and are selected from the group consisting of benzoates, lactates, maleates, citrates and octanoates of primary alcohols having from 12 to 15 carbon atoms.

3. A make-up remover according to claim 2 comprising a mixture of said benzoate and octanoate esters.

4. A make-up remover according to claim 1 consisting exclusively of the ingredients recited therein together with formulants selected from the group consisting of innocuous cosmetological solvents and co-solvents, colorants and extenders.

5. A make-up remover according to claim 1 which further comprises up to 25% by weight of a liquid triester of a lower aliphatic tribasic carboxylic acid as a co-solvent.

6. A make-up remover according to claim 5 wherein the co-solvent is a trioctyl citrate.

7. A make-up remover according to claim 1 which is substantially oil- and grease-free wherein additional materials that are capable of leaving an oily or greasy residue are substantially or completely excluded.

8. A make-up remover according to claim 1 wherein the cyclomethicone compound is a compound of formula

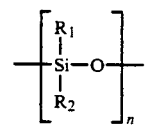

in which $R_1$ and $R_2$ is each lower alkyl having from one to four carbon atoms with or without innocuous substituents selected from the group consisting of halo, hydroxyl, carboxyl or methoxy and n is from 3 to 6; which compounds are cyclized.

9. A make-up remover according to claim 8 wherein said cyclomethicone compound is octamethylcyclotetrasiloxane or decamethylcyclopentasiloxane.

10. A make-up remover according to claim 1 being essentially free of any detergent or surfactant and being substantially non-stinging to the eyes.

11. A make-up remover according to claim 1 comprising, on a weight basis, from 60 to 97 percent of said cyclomethicone material, from 5 to 25 percent of said ester or esters and from 1 to 15 percent of a co-solvent for said makeup being a liquid triester of a lower aliphatic tribasic carboxylic acid.

12. A non-aqueous, oil-free make-up remover consisting essentially, on a weight basis, of from 60 to 97 percent of a cyclomethicone of formula

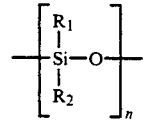

in which $R_1$ and $R_2$ is each lower alkyl having from one to four carbon atoms with or without innocuous substituents selected from the group consisting of halo, hydroxyl, carboxyl or methoxy and n is from 3 to 6, or a mixture of cyclomethicones having said formula, with from 5 to 25 percent of a cosmetologically acceptable substantially non-oily ester or esters selected from the group consisting of benzoates and octanoates of primary alcohols having from 12 to 15 carbon atoms said ester or esters being miscible with said cyclomethicone material and being effective in stabilizing said cyclomethicone against evaporative losses, said makeup remover further comprising from 1 to 15 percent by weight of co-solvent for said make-up being a liquid triester of a lower aliphatic tribasic carboxylic acid, the balance, if any, comprising one or more formulants selected from the group consisting of innocuous cosmetological solvents and co-solvents, colorants, fragrances and extenders.

* * * * *